(12) United States Patent
Lim

(10) Patent No.: US 11,911,314 B2
(45) Date of Patent: Feb. 27, 2024

(54) PORTABLE DEVICE FOR ATTACHING CONTACT LENS TO THE EYE

(71) Applicant: Chae Young Lim, Gimpo-si (KR)

(72) Inventor: Chae Young Lim, Gimpo-si (KR)

( * ) Notice: Subject to any disclaimer, the term of this patent is extended or adjusted under 35 U.S.C. 154(b) by 743 days.

(21) Appl. No.: 17/078,260

(22) Filed: Oct. 23, 2020

(65) Prior Publication Data

US 2021/0386585 A1    Dec. 16, 2021

(30) Foreign Application Priority Data

Jun. 10, 2020    (KR) .................. 20-2020-0002013

(51) Int. Cl.
*A61F 9/00*    (2006.01)

(52) U.S. Cl.
CPC .................. *A61F 9/0061* (2013.01)

(58) Field of Classification Search
CPC .......................... A61F 9/0061; A61B 17/0231
USPC ...................... 606/107; 81/9.3, 420; 600/236
See application file for complete search history.

(56) References Cited

U.S. PATENT DOCUMENTS

2020/0069301 A1*    3/2020  Kent .................. A61B 17/0231

FOREIGN PATENT DOCUMENTS

| KR | 200330914 Y1 | | 10/2003 |
| KR | 1020110095568 A | | 8/2011 |
| KR | 20170019282 | * | 2/2017 |
| KR | 101947772 B1 | | 2/2019 |

* cited by examiner

*Primary Examiner* — Thomas McEvoy
(74) *Attorney, Agent, or Firm* — GREER BURNS & CRAIN, LTD.

(57) ABSTRACT

A portable device for attaching a contact lens to an eye includes a first clamp including a first grip portion having a first grip hole and a first arm including two branches extending from the first grip portion, each branch extending obliquely and being bent, and a second clamp having a shape identical to the shape of the first clamp, the second clamp including a second grip portion having a second grip hole and a second arm, wherein the first arm and the second arm are coupled to each other so as to intersect each other about a pivot point, and a first eye opening means and a second eye opening means are installed at tip ends of the first arm and the second arm, respectively, each eye opening means being configured to be brought into tight contact with a corresponding eyelid.

1 Claim, 3 Drawing Sheets

PORTABLE DEVICE FOR ATTACHING CONTACT LENS TO THE EYE

BACKGROUND OF THE INVENTION

Field of the Invention

The present invention relates to a device for attaching a contact lens to an eye, and more particularly to a portable device capable of easily and sanitarily attaching a contact lens to an eye.

Description of the Related Art

In general, a contact lens is attached to the cornea of an eye in order to correct eyesight or to remedy the eye or for the purpose of beauty. The Korean eyewear industry states and statistics in the year of 2017 reveal that the percentage of Korean adults who simultaneously use glasses and contact lenses is 8.5% and that the number of users who use contact lenses has gradually increased over the years. Also, in recent years, the use of contact lenses by, particularly, students and young people has rapidly increased due to an increase in leisure time and an increase in various media such as social network services (SNSs). Meanwhile, in the case in which contact lenses are attached to and detached from eyes using fingers of a user, such attachment and detachment are inconvenient and the contact lenses may be contaminated. For these reasons, the demand for a tool or device capable of sanitarily attaching and detaching contact lenses has also increased with an increase in use of contact lenses. As a conventional contact lens wearing device, examples of an integrated device including an eye opening means configured to open eyelids and a wearing means configured to move a contact lens held thereby toward the cornea of an eye are disclosed in Korean Registered Utility Model No. 20-0330914, Korean Registered Patent No. 10-1947772, and Korean Patent Application Publication No. 10-2011-0095568. However, these devices have problems in that the structure of the devices is complicated, whereby manufacturing cost of the devices is high and the devices frequently malfunction.

SUMMARY OF THE INVENTION

The present invention has been made in view of the above problems, and it is an object of the present invention to provide a portable device for attaching a contact lens to an eye that is capable of naturally, stably, and easily opening the eye.

It is another object of the present invention to provide a portable device for attaching a contact lens to an eye that is capable of lifting an upper eyelash during opening of the eye, whereby it is possible to prevent interference with the upper eyelash and to prevent foreign matter from being introduced into the eye.

In accordance with the present invention, the above and other objects can be accomplished by the provision of a portable device for attaching a contact lens to an eye, the portable device including a first clamp including a first grip portion having a first grip hole, in which a finger of a user is located, formed therein and a first arm including two branches extending from the first grip portion so as to be opposite each other in the state of being spaced apart from each other, each branch extending obliquely and being bent, and a second clamp having a shape identical to the shape of the first clamp, the second clamp including a second grip portion having a second grip hole formed therein and a second arm, wherein the first arm and the second arm are coupled to each other so as to intersect each other about a pivot point in the state of being opposite each other, and a first eye opening means and a second eye opening means are installed at tip ends of the first arm and the second arm, respectively, each of the first eye opening means and the second eye opening means being configured to be brought into tight contact with a corresponding one of eyelids.

In an embodiment of the present invention, the first eye opening means may include a curved upper closed arc member and an upper arc finish member coupled to an open end of the upper closed arc member, and the second eye opening means may include a lower closed arc member having a shape corresponding to the shape of the upper closed arc member and a lower arc finish member coupled to an open end of the lower closed arc member.

In an embodiment of the present invention, the upper closed arc member may be provided on the upper surface thereof with a curved protrusion configured to lift an upper eyelash at the time of opening the eye.

In an embodiment of the present invention, each of the first eye opening means and the second eye opening means may be made of a silicone material.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, embodiments of the present invention will be described in detail with reference to the accompanying drawings such that the present invention can be easily embodied by a person having ordinary skill in the art to which the present invention pertains. However, the present invention may be embodied in various different forms, and is not limited to the embodiments described herein. In order to clearly describe the present invention, parts having no relation to the description are omitted from the drawings. Wherever possible, the same reference numbers will be used throughout the drawings to refer to the same or like parts.

In the case in which a part "includes" a component in this specification, this means that the part may not exclude another component but may further include another component unless mentioned otherwise.

Figure 1:
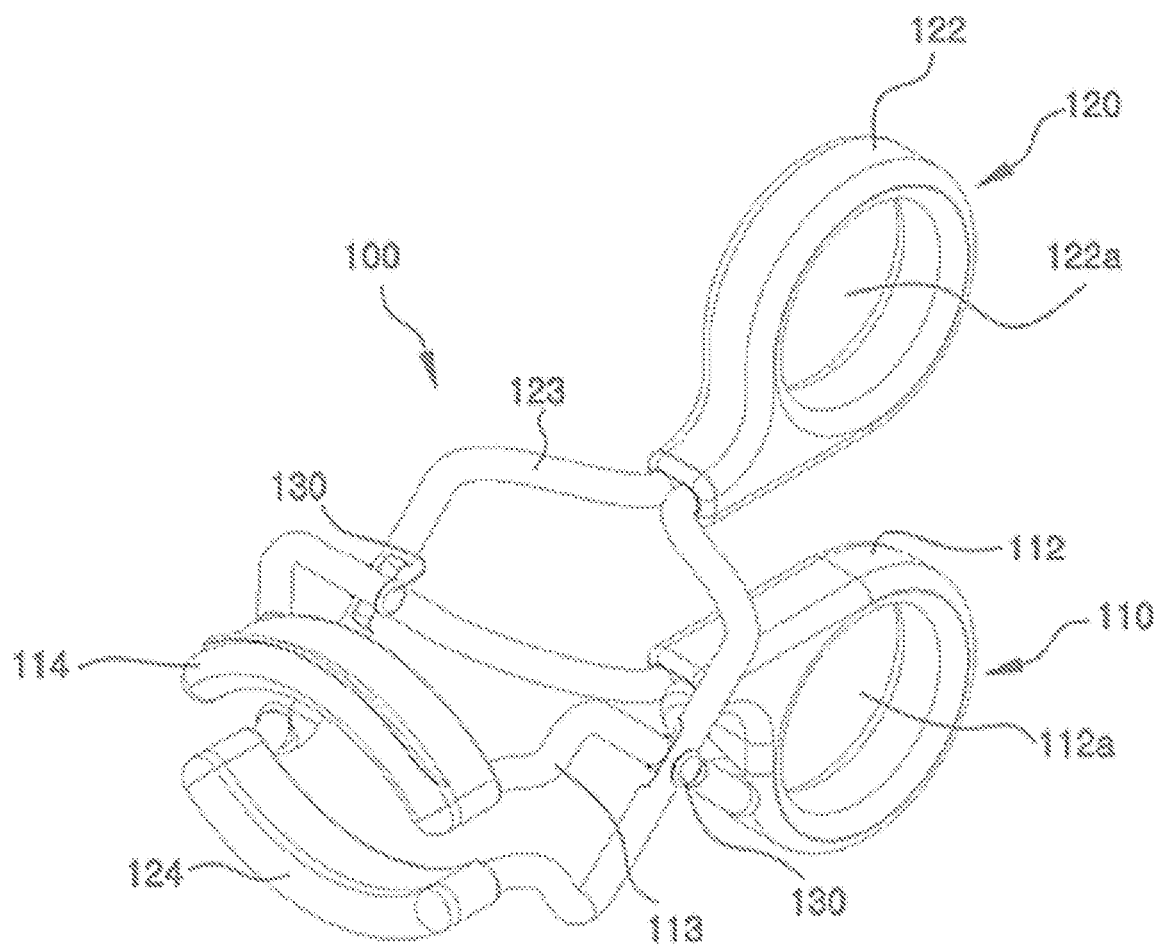
FIG. 1 is a perspective view of a portable device for attaching a contact lens to an eye according to an embodiment of the present invention.
Figure 2:
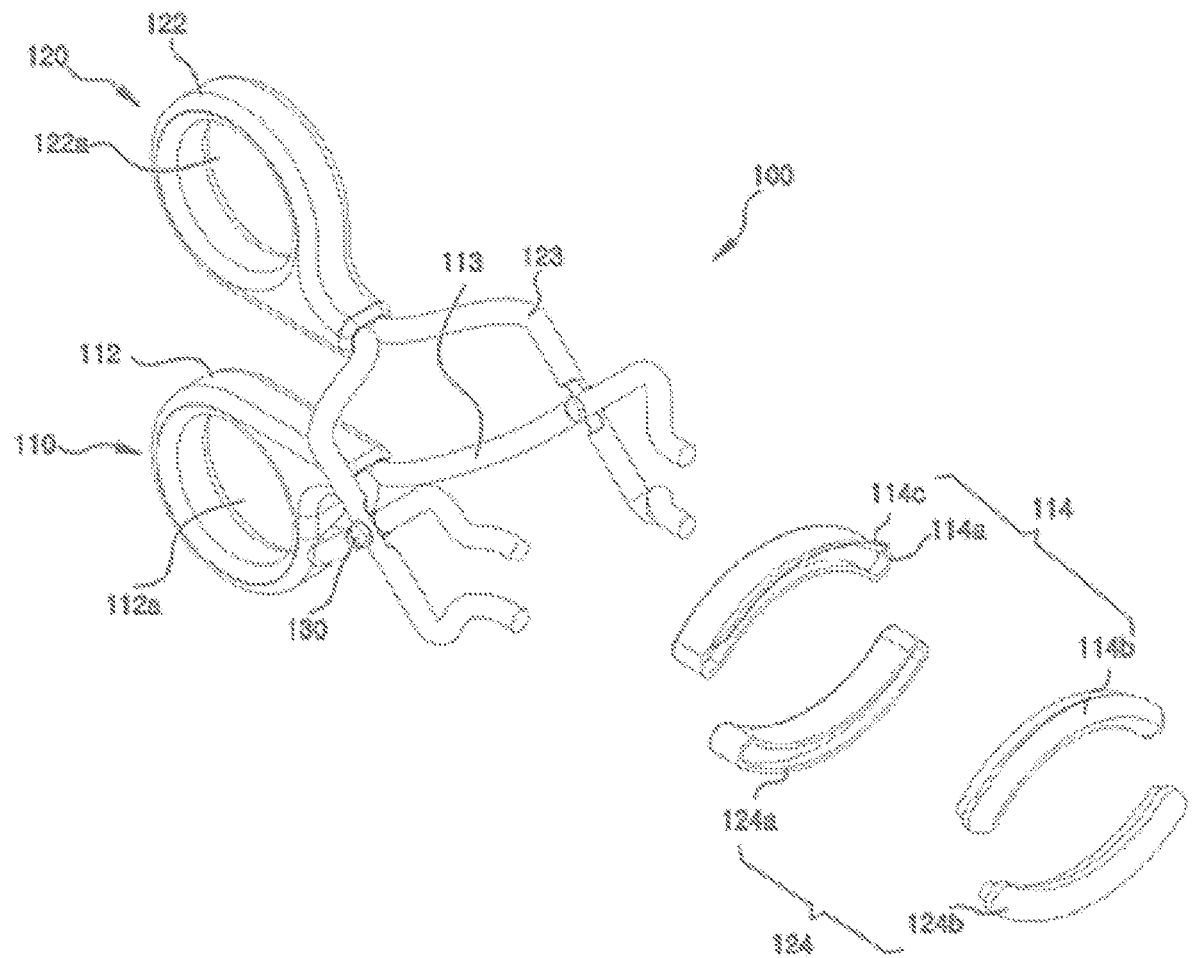
FIG. 2 is an exploded perspective view of the portable device for attaching the contact lens to the eye according to the embodiment of the present invention.
Figure 3A:
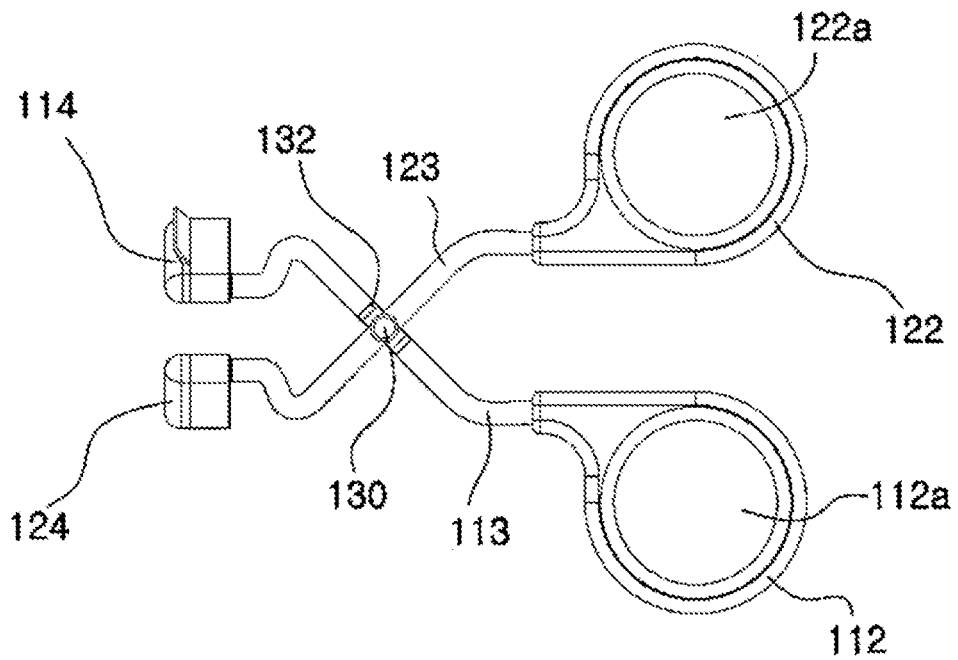
FIGS. 3A and 3B are side views showing the use states of the portable device for attaching the contact lens to the eye according to the embodiment of the present invention.
Figure 3B:
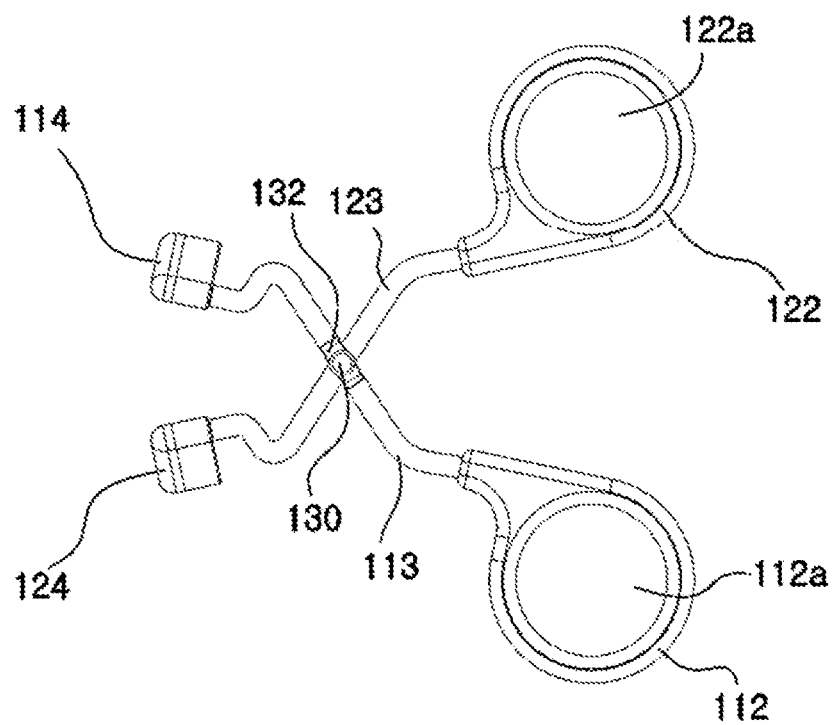

FIG. 1 is a perspective view of a portable device for attaching a contact lens to an eye according to an embodiment of the present invention, FIG. 2 is an exploded perspective view of the portable device for attaching the contact lens to the eye according to the embodiment of the present invention, and FIGS. 3A and 3B are side views showing the use states of the portable device for attaching the contact lens to the eye according to the embodiment of the present invention.

As shown in FIGS. 1 and 2, the portable device 100 for attaching the contact lens to the eye, which is a device that enables a user to open eyelids without directly laying their hand on the eyelids, may mainly include a first clamp 110, a second clamp 120, a first eye opening means 114 installed at the first clamp 110, and a second eye opening means 124 installed at the second clamp 120.

In general, the first clamp 110 and the second clamp 120 are coupled to each other so as to intersect each other about a pivot point 130 in order to open the eyelids in an upward-downward direction by increasing or decreasing the angle therebetween.

A first grip portion 112 having a first circular grip hole 112a, through which a finger is inserted to grip the first grip portion 112, formed therein is installed at one end of the first clamp 110. A first arm 113, made of any one of a metal material and a synthetic resin material, may be connected to the first grip portion 112.

The first arm 113 includes two branches extending from the first grip portion 112 so as to be opposite each other in the state of being spaced apart from each other. Each branch of the first arm 113 has a shape in which the branch extends parallel to the first grip portion 112, is bent upwards at an angle of about 45 degrees, extends a predetermined length, is bent in a V shape, and extends parallel to the first grip portion 112.

The first eye opening means 114, configured to be brought into tight contact with a corresponding one of the eyelids, may be installed at the tip end of the first arm 113.

Ends of the two branches of the first arm 113, which are opposite each other, are inserted into a curved upper closed arc member 114a of the first eye opening means 114. An upper arc finish member 114b may be coupled to an open end of the upper closed arc member 114a, i.e. the front end of the upper closed arc member 114a.

Each of the upper closed arc member 114a and the upper arc finish member 114b may be made of a silicone material in order to prevent skin damage and to achieve soft but tight contact. In addition, a curved protrusion 114c, configured to lift an upper eyelash at the time of opening the eye, may be formed on the upper surface of the upper closed arc member 114a.

The curved protrusion 114c is formed so as to have a length equal to or slightly less than the arc length of the upper closed arc member 114a. The curved protrusion 114c may have a flap shape that faces upwards.

The second clamp 120, which is installed so as to intersect the first clamp 110, is made of the same material as the first clamp 110 and is manufactured so as to have the same shape as the first clamp 110. The second clamp 120 is coupled to the pivot point 130 in a direction in which the second clamp 120 is opposite the first clamp 110.

A second grip portion 122 having a second circular grip hole 122a, through which a finger is inserted to grip the second grip portion 122, formed therein is installed at one end of the second clamp 120. A second arm 123, made of any one of a metal material and a synthetic resin material, may be connected to the second grip portion 122.

The second arm 123 includes two branches extending from the second grip portion 122 so as to be opposite each other in the state of being spaced apart from each other. Each branch of the second arm 123 has a shape in which the branch extends parallel to the second grip portion 122, is bent downwards at an angle of about 45 degrees, extends a predetermined length, is bent in a V shape, and extends parallel to the second grip portion 122.

The pivot point 130 is a portion at which the first arm 113 and the second arm 123 are connected to each other so as to intersect each other. Preferably, the pivot point 130 is rotatably installed at the middle of the inclined portion of each of the first arm 113 and the second arm 123.

The second eye opening means 124, configured to be brought into tight contact with a corresponding one of the eyelids, may be installed at the tip end of the second arm 123.

Ends of the two branches of the second arm 123 are inserted into a curved lower-closed arc member 124a of the second eye opening means 124. A lower arc finish member 124b may be coupled to an open end of the lower closed arc member 124a.

Each of the lower closed arc member 124a and the lower arc finish member 124b may be made of a silicone material in order to prevent skin damage and to achieve soft but tight contact.

Meanwhile, in another embodiment of the present invention, as shown in FIGS. 3A and 3B, a stopper surface 132 having a different thickness is formed on any one of the first arm 113 and the second arm 123 so as to be located about the pivot point 130 in order to limit the opening angle between the first arm 113 and the second arm 123 when the first arm 113 and the second arm 123 are opened.

That is, the stopper surface 132, which preferably has a smaller thickness, comes into contact with the first arm 113 or the second arm 123 when the first arm 113 and the second arm 123 are opened to a predetermined angle or more in order to prevent further rotation thereof, whereby it is possible to maintain a stable open state.

The operation of the portable device for attaching the contact lens to the eye according to the present invention, configured as described above, will be described with reference to FIGS. 3A and 3B.

As shown in FIGS. 3A and 3B, the index finger of one hand of a user is inserted through the second grip hole 122a, and the thumb of the hand is located in the first grip hole 112a. Subsequently, based on an eye of the user, the second eye opening means 124 is brought into tight contact with an under-eye portion, and the first eye opening means 114 is located at an eyelid.

Subsequently, force is applied to the index finger and the thumb in order to increase the distance between first grip hole 112a and the second grip hole 122a. As a result, the first arm 113 and the second arm 123 are opened about the pivot point 130, and the eyelid is lifted by the upper closed arc member 114a and the upper arc finish member 114b of the first eye opening means 114. At this time, an upper eyelash is lifted by the curved protrusion 114c, in the same manner as when the eyelid is lifted.

In the state in which the eye is stably open, as described above, the user attaches a contact lens to the eye while holding the contact lens in the other hand.

When attachment of the contact lens to the eye is completed, the user immediately removes the portable device 100 from their face.

In the case in which the user wishes to separate the contact lens from the eye, the user brings the portable device 100 into tight contact with the circumference of the eye in the state in which the first grip portion 112 and the second grip portion 122 are gripped using the thumb and the index finger, opens the eye, and separates the contact lens from the eye, in the same manner as in the case in which the user attaches the contact lens to the eye.

Based on the functions described above, the eye is opened by a pair of arms, which is interlocked with an ordinary operation of spreading fingers, and then the contact lens is attached to the eye, whereby it is possible to stably attach the contact lens to the eye.

In addition, the upper eyelash is lifted by the curved protrusion during opening of the eye, whereby it is possible to prevent interference with the upper eyelash and to prevent foreign matter from being introduced into the eye.

As is apparent from the above description, the portable device for attaching the contact lens to the eye according to the present invention has an effect in that the eye is opened by a pair of arms, which is interlocked with an ordinary operation of spreading fingers, and then the contact lens is attached to the eye, whereby it is possible to stably attach the contact lens to the eye.

In addition, the portable device for attaching the contact lens to the eye according to the present invention has an effect in that the upper eyelash is lifted by the curved protrusion during opening of the eye, whereby it is possible to prevent interference with the upper eyelash and to prevent foreign matter from being introduced into the eye.

Although the specific embodiments of the present invention have been described in detail above, it is obvious that the present invention can be implemented in various other embodiments without departing from the scope of the invention. Therefore, the scope of the present invention is not defined by the embodiments described above but is defined by the accompanying claims and equivalents thereto.

What is claimed is:

1. A portable device for attaching a contact lens to an eye, the portable device comprising:

a first clamp comprising a first grip portion having a first grip hole, in which a finger of a user is located, formed therein and a first arm comprising two branches extending from the first grip portion so as to be opposite each other in a state of being spaced apart from each other, each branch extending obliquely and being bent; and a second clamp having a shape identical to a shape of the first clamp, the second clamp comprising a second grip portion having a second grip hole formed therein and a second arm, wherein the first arm and the second arm are coupled to each other so as to intersect each other about a pivot point in a state of being opposite each other, wherein a first eye opening means and a second eye opening means are installed at tip ends of the first arm and the second arm, respectively, each of the first eye opening means and the second eye opening means being configured to be brought into tight contact with a corresponding one of eyelids, wherein the first eye opening means is convexly curved upward, wherein the second eye opening means is convexly curved downward, wherein the first eye opening means comprises a curved upper closed arc member and an upper arc finish member coupled to the front end of the upper closed arc member, wherein the second eye opening means comprises a lower closed arc member having a shape corresponding to a shape of the upper closed arc member and a lower arc finish member coupled to the front end of the lower closed arc member, wherein the upper closed arc member is provided on an upper surface thereof with a curved protrusion configured to lift an upper eyelash at a time of opening the eye, wherein the curved protrusion has a flap that faces upwards, wherein each of the upper arc finish member and the lower arc finish member are made of a silicone material.

* * * * *